US012582445B1

(12) United States Patent
Bin Suhaym et al.

(10) Patent No.: US 12,582,445 B1
(45) Date of Patent: Mar. 24, 2026

(54) APPARATUS FOR ORTHOGNATHIC SURGICAL PLANNING

(71) Applicant: KING SAUD UNIVERSITY, Riyadh (SA)

(72) Inventors: Omar Abdullah Bin Suhaym, Riyadh (SA); Hissah Saleh Alshalawi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/339,239

(22) Filed: Sep. 24, 2025

Related U.S. Application Data

(63) Continuation of application No. 19/332,914, filed on Sep. 18, 2025, now abandoned.

(51) Int. Cl.
    A61B 17/66 (2006.01)
(52) U.S. Cl.
    CPC ................................. A61B 17/663 (2013.01)
(58) Field of Classification Search
    CPC .......... A61B 17/66; A61B 17/663; A61C 7/10
    See application file for complete search history.

(56) References Cited

U.S. PATENT DOCUMENTS

| | | | |
|---|---|---|---|
| 6,102,698 A | * | 8/2000 | Staples .................. A61C 11/00 |
| | | | 433/56 |
| 6,592,366 B2 | | 7/2003 | Triaca et al. |
| 10,973,614 B2 | | 4/2021 | Scommegna et al. |

FOREIGN PATENT DOCUMENTS

| | | | | |
|---|---|---|---|---|
| CN | 107468359 A | * | 12/2017 | ............... A61C 7/08 |
| DE | 2722515 A1 | | 5/1981 | |
| EP | 3354226 B1 | * | 3/2021 | ............... A61C 7/10 |
| WO | 2014/170500 A1 | | 10/2014 | |

* cited by examiner

*Primary Examiner* — Si Ming Ku
(74) *Attorney, Agent, or Firm* — Nath, Goldberg & Meyer; Joshua B. Goldberg

(57) ABSTRACT

An apparatus for orthognathic surgical planning includes a base plate and a central pillar mounted to the base plate. An anterior plate, first posterior plate, and second posterior plate are provided as top plates mounted above the base plate. The top plates include respective linear adjustment screws, vertical adjustment screws, and ball joints permitting multi-dimensional adjustment. The ball joints may be fixed in position by respective locking screws. The top plates include respective magnets onto which may be fastened maxillary casts used in pre-surgical planning of, in particular, a Le Fort I three-piece segmented osteotomy procedure. The apparatus reduces time required for pre-surgical planning as well as the risk of errors during maxillary segment repositioning.

9 Claims, 6 Drawing Sheets

APPARATUS FOR ORTHOGNATHIC SURGICAL PLANNING

CROSS-REFERENCE TO RELATED APPLICATION

This application is a continuation of U.S. patent application Ser. No. 19/332,914, filed on Sep. 18, 2025, the entire contents of which are incorporated herein by reference.

BACKGROUND

Field

The disclosure of the present patent application relates to an apparatus for orthognathic surgical planning, and particularly to an apparatus for three-piece segmented maxillary alignment in the case of a Le Fort I maxillary osteotomy.

Description of Related Art

Orthognathic surgery (also known as corrective jaw surgery) is pivotal in addressing complex dentofacial deformities, necessitating precise diagnostic techniques and meticulous planning to predict and achieve desired jaw movements. Traditional approaches, including face-bow transfers, bite registrations, and plaster model adjustments, although widely practiced, are inherently labor-intensive and vulnerable to cumulative procedural inaccuracies.

One of the most challenging aspects of orthognathic surgery arises during Le Fort I maxillary osteotomy, a surgical procedure in which the upper jaw (maxilla) is cut and separated from the rest of the facial skeleton. A cut is made above the teeth, at the level of the Le Fort I fracture line, allowing a surgeon to reposition the entire upper jaw. Such a procedure may be used to correct severe malocclusion (misaligned bite), an open bite, crossbite, or facial asymmetry. In some cases, a three-piece segmentation of the maxilla is required. In such instances, manual segment placement frequently results in inaccuracies, misalignment, and procedural inefficiencies. Current methodologies demand extensive manual intervention and lack precise mechanisms for controlled segment alignment, elevating the risk of errors.

Thus, an apparatus for orthognathic surgical planning solving the aforementioned problems is desired.

SUMMARY

The apparatus for orthognathic surgical planning provided by the present disclosure presents a novel solution to the shortcomings of the prior art. By integrating multidimensional adjustment and stabilization mechanisms, the apparatus offers surgeons a tool that ensures desired outcomes and streamlines surgical workflows.

The apparatus for orthognathic surgical planning includes a base plate and a central pillar mounted to the base plate. An anterior plate is provided and an anterior screw extending through the anterior plate into the central pillar. The anterior plate is linearly movable along the anterior screw by rotation of the anterior screw. A length of the anterior screw extends in an anterior-posterior axis. Further provides is a first posterior plate is and a first posterior screw extending through the first posterior plate into the central pillar. The first posterior plate is linearly movable along the first posterior screw by rotation of the first posterior screw. A length of the first posterior screw extends in a transverse axis orthogonal to the anterior-posterior axis. A second posterior plate is provided and a second posterior screw extending through the second posterior plate into the central pillar. The second posterior plate is linearly movable along the second posterior screw by rotation of the second posterior screw. A length of the second posterior screw extends in the transverse axis.

An anterior magnet, first posterior magnet, and second posterior magnet may be included on respective top faces of the anterior plate, first posterior plate, and second posterior plate.

The apparatus for orthognathic surgical planning may further include an anterior ball joint, first posterior ball joint, and second posterior ball joint on which are respectively mounted the anterior plate, first posterior plate, and second posterior plate. The apparatus for may include an anterior sliding track, a first posterior sliding track, and a second posterior sliding track on which are respectively mounted the anterior ball joint, first posterior ball joint, and second posterior ball joint. The anterior sliding track, first posterior sliding track, and second posterior sliding track may be mounted to the central pillar.

The apparatus for orthognathic surgical planning may include an anterior locking screw, a first posterior locking screw, and a second posterior locking screw, which are respectively configured to hold the anterior ball joint, first posterior ball joint, and the second posterior ball joint in a fixed position.

An anterior vertical adjustment screw and an anterior support arm may be included. The anterior support arm may be mounted to the anterior ball joint. The anterior vertical adjustment screw is freely rotatable within a bottom surface of the anterior plate and is in threaded engagement with the anterior support arm.

A first posterior vertical adjustment screw may be included and a first posterior support arm. The first posterior support arm may be mounted to the first posterior ball joint. The first posterior vertical adjustment screw is freely rotatable within a bottom surface of the first posterior plate and is in threaded engagement with the first posterior support arm.

A second posterior vertical adjustment screw may be included and a second posterior support arm. The second posterior support arm may be mounted to the second posterior ball joint. The second posterior vertical adjustment screw is freely rotatable within a bottom surface of the second posterior plate and is in threaded engagement with the second posterior support arm. The anterior vertical adjustment screw, first posterior vertical adjustment screw, and the second posterior vertical adjustment screw may be spring-loaded.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1A:
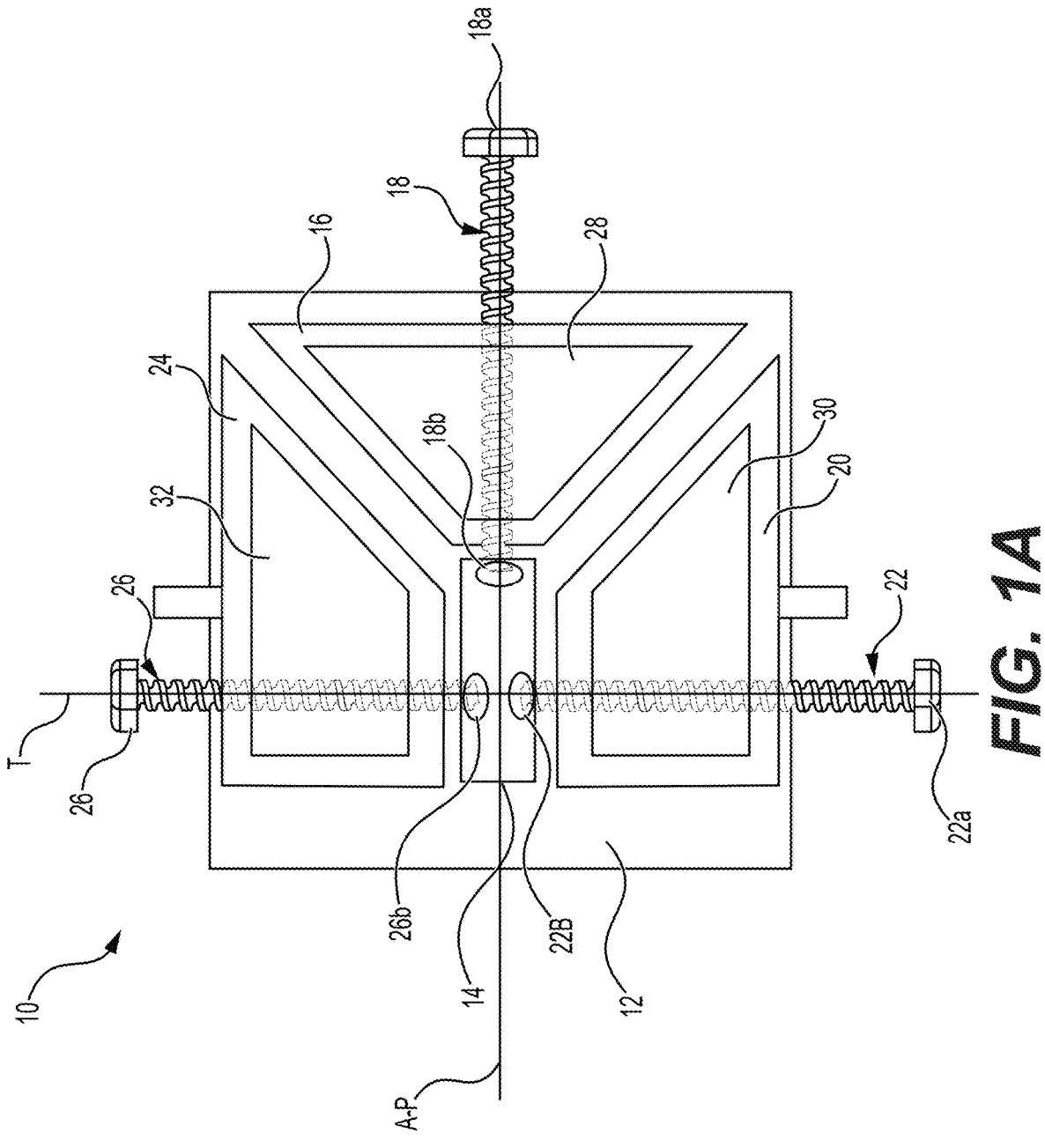
FIG. 1A is a top view of an apparatus for orthognathic surgical planning.
Figure 1B:
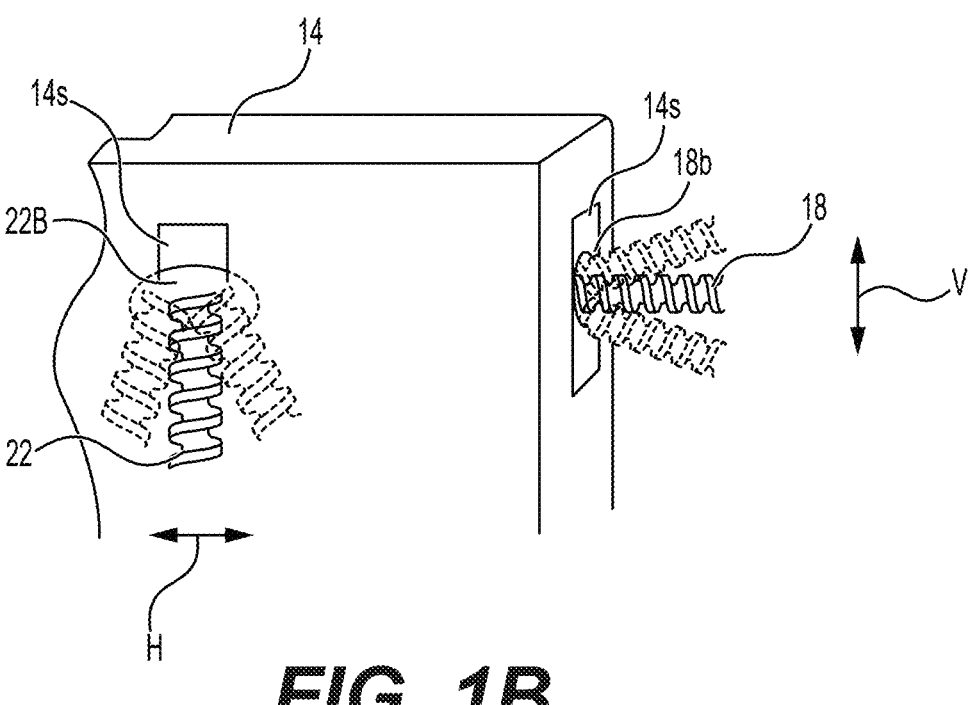
FIG. 1B is a perspective view of a central pillar and distal ends of a first posterior screw and an anterior screw.
Figure 1C:
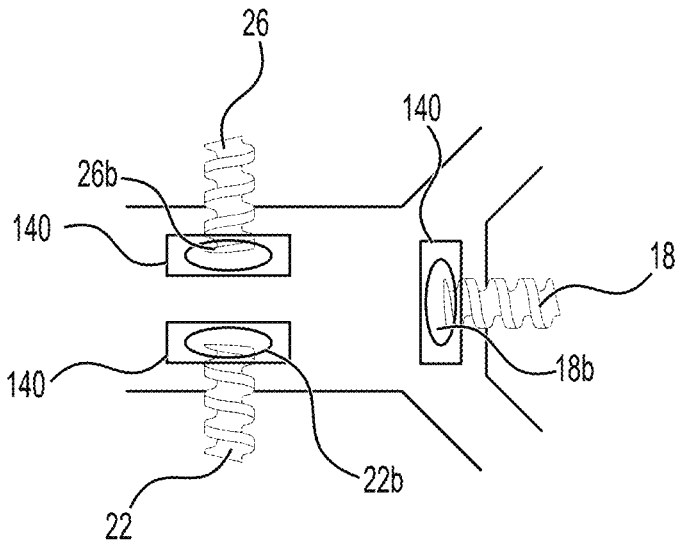
FIG. 1C is a top view of multiple pillars used to anchor distal ends of an anterior screw, a first posterior screw, and a second posterior screw.

With reference to FIGS. 1A-C, the apparatus 10 for orthognathic surgical planning provided by the present disclosure includes a base plate 12 and a central pillar 14 mounted to the base plate 12. An anterior plate 16 is provided and an anterior screw 18 extends through the anterior plate 16 into the central pillar 14. The anterior plate 16 is linearly movable along the anterior screw 18 by rotation of the anterior screw 18. A length of the anterior screw 18 extends along an anterior-posterior axis A-P. A first posterior plate 20 is provided and a first posterior screw 22 extends through the first posterior plate 20 into the central pillar 14. The first posterior plate 20 is linearly movable along the first posterior screw 22 by rotation of the first posterior screw 22. A length of the first posterior screw 22 extends along a transverse axis T orthogonal to the anterior-posterior axis A-P. A second posterior plate 24 is provided and a second posterior screw 26 extends through the second posterior plate 24 into the central pillar 14. The second posterior plate 24 is linearly movable along the second posterior screw 26 by rotation of the second posterior screw 26. A length of the first posterior screw 22 along the transverse axis T. As used herein, the anterior plate 16, first posterior plate 20, and second posterior plate 24 may be collectively referred to as the "top plates (16, 20, 24)". The anterior screw 18, first posterior screw 22, and second posterior screw 26 may be collectively referred to herein as the "adjustment screws (18, 22, 26)".

With further reference to FIGS. 1A-C, an anterior magnet 28, a first posterior magnet 30, and a second posterior magnet 32 (collectively referred to herein as "the magnets (28, 30, 32)") may be included respectively on the anterior plate 16, first posterior plate 20, and second posterior plate 24. The magnets (28, 30, 32) serve to hold respective cast segments in place during pre-surgical planning, which will be described in more detail below with reference to FIG. 3.

With further reference to FIG. 1, the anterior screw 18, first posterior screw 22 and second posterior screw 26 include respective heads 18a, 22a, 26a (collectively referred to herein as "heads (18a, 22a, 26a)"), and freely rotatable and enlarged distal ends 18b, 22b, 26b (collectively referred to herein as "distal ends (18b, 22b, 26b)") mounted within central pillar 14. The heads (18a, 22a, 26a) each are configured to be gripped by hand and rotated, while the distal ends (18b, 22b, 26b) each are engaged with central pillar 14.

Turning to FIG. 1B, central pillar 14 may include slots 14s for receiving respective distal ends (18b, 22b, 26b) of the anterior screw 18, first posterior screw 22, and second posterior screw 26. Slots 14s are sized slightly larger than the threaded width of the adjustment screws (18, 22, 26), but narrower than the enlarged distal ends (18b, 22b, 26b) of the adjustment screws (18, 22, 26), such that some horizontal movement/adjustability H as well as vertical adjustability V by the adjustment screws (18, 22, 26) is permitted, as well as by the top plates (16, 20, 24) attached thereto. Distal ends (18b, 22b, 26b) may be of any suitable shape, but in particular could be formed as spheres or balls which are wider than the slots 14s. Other non-limiting suitable shapes for the distal ends (18b, 22b, 26b) might include discs or blocks, among others.

In the embodiment of FIG. 1A, while a single central pillar 14 is shown, it should be understood that respective individual pillars 140 could be used, as shown in FIG. 1C, for each of the adjustment screws (18, 22, 26).

Figure 2A:
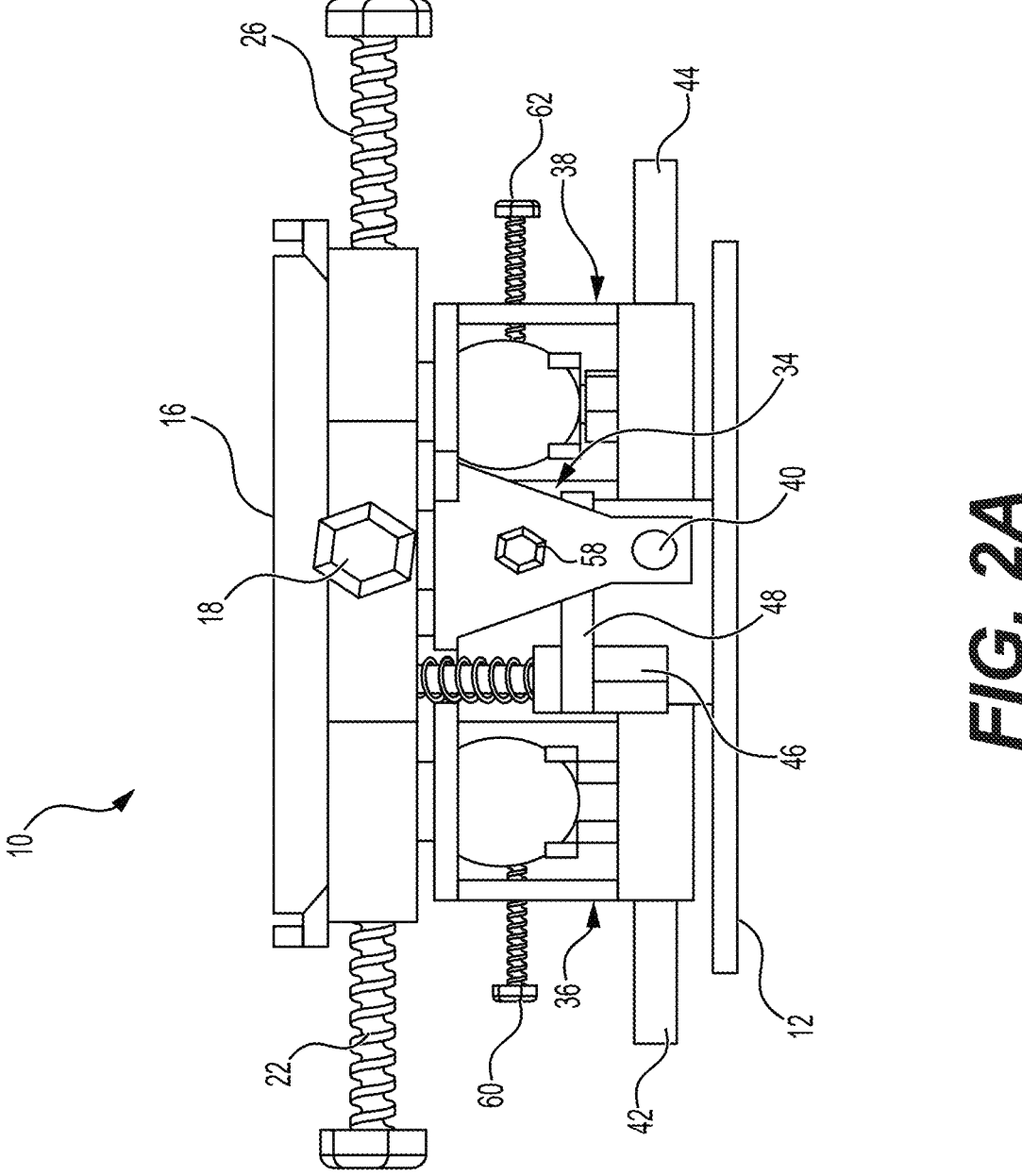
FIG. 2A is a front view of an apparatus for orthognathic surgical planning.
Figure 2B:
FIG. 2B is a rear perspective view of an apparatus for orthognathic surgical planning.
Figure 2C:
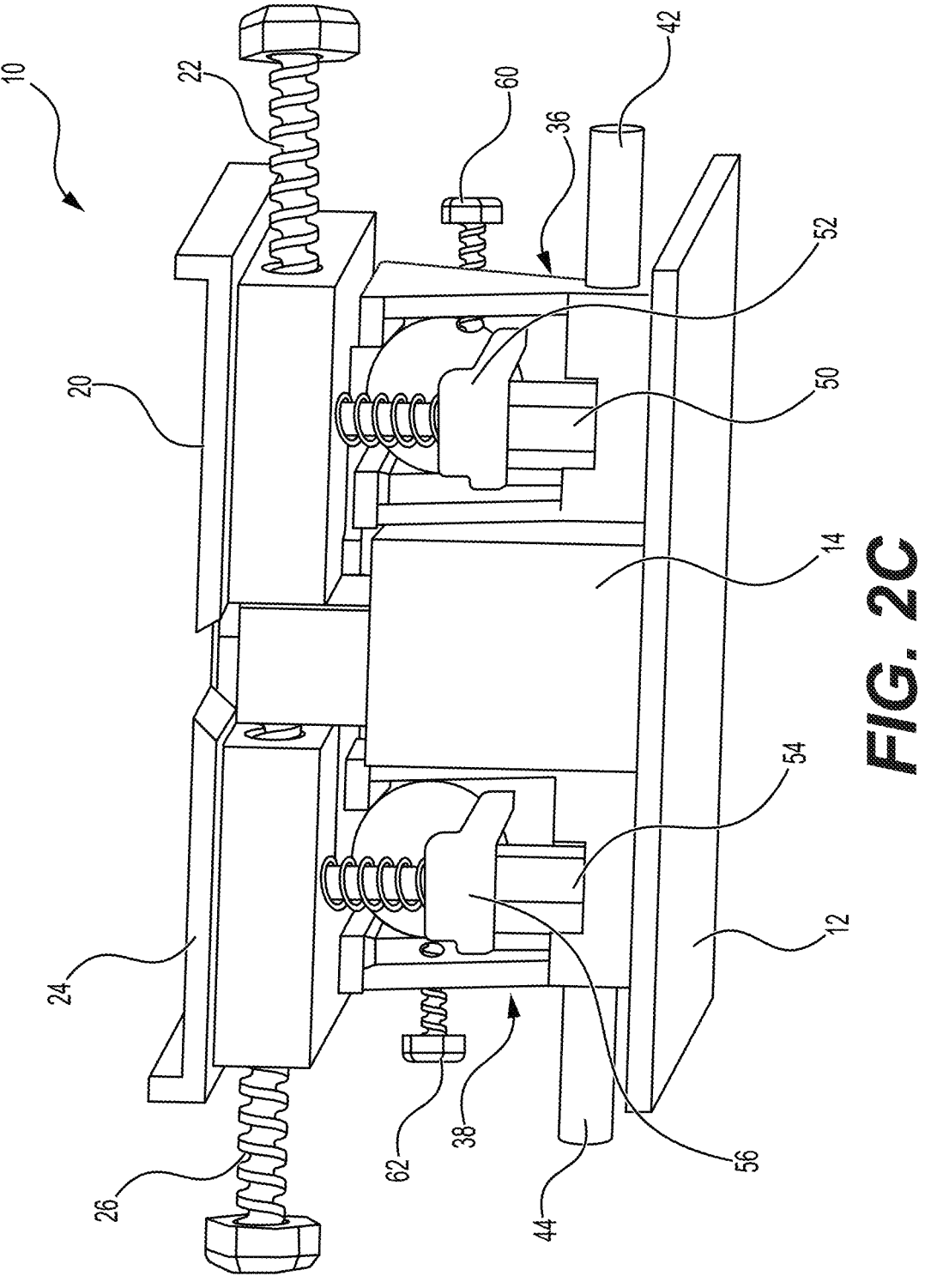
FIG. 2C is a rear view of an apparatus for orthognathic surgical planning.

With reference to FIGS. 2A-C, the apparatus for orthognathic surgical planning may further include an anterior ball joint 34 (shown in FIG. 2A), a first posterior ball joint 36, and a second posterior ball joint 38 on which the anterior plate 16, first posterior plate 20, and second posterior plate 24 are respectively mounted. The apparatus may further include an anterior sliding track 40 (shown in FIG. 2A), a first posterior sliding track 42, and a second posterior sliding track 44 on which the anterior ball joint 34, first posterior ball joint 36, and the second posterior ball joint 38 are respectively mounted. Collectively, the anterior ball joint 34, the first posterior ball joint 36, and the second posterior ball joint 38 may be referred to herein as the "ball joints (34, 36, 38)." The anterior sliding track 40, first posterior sliding track 42, and second posterior sliding track 44 may be mounted to the central pillar 14. Collectively, the anterior sliding track 40, first posterior sliding track 42 and second posterior sliding track 44 may be referred to herein as the "sliding tracks (40, 42, 44)."

It should be understood that the shapes illustrated of the ball joints (34, 36, 38) and that of the sliding tracks (40, 42, 44) are non-limiting and other shapes/types of ball joints and sliding tracks may be used. For example, although not shown, the sliding tracks (40,42,44) could be formed in the base plate 12 of the apparatus 10, rather than mounted to the central pillar 14.

With further reference to FIGS. 2A-C, an anterior vertical adjustment screw 46 (seen in FIG. 2A) and an anterior support arm 48 may be included. The anterior support arm 48 may be mounted to the anterior ball joint 34. The anterior vertical adjustment screw 46 is freely rotatable within a bottom surface of the anterior plate 16 and is in threaded engagement with the anterior support arm 48.

A first posterior vertical adjustment screw 50 (seen in FIGS. 2C, 2B) and a first posterior support arm 52 may be included. The first posterior support arm 52 may be mounted to the first posterior ball joint 36. The first posterior vertical adjustment screw 50 is freely rotatable within a bottom surface of the first posterior plate 20 and is in threaded engagement with the first posterior support arm 52.

A second posterior vertical adjustment screw 54 and a second posterior support arm 56 may be included. The second posterior support arm 56 may be mounted to the second posterior ball joint 38. The second posterior vertical adjustment screw 54 is freely rotatable within a bottom surface of the second posterior plate 24 and is in threaded engagement with the second posterior support arm 56.

Collectively, the anterior vertical adjustment screw 46, first posterior vertical adjustment screw 50, and second posterior vertical adjustment screw 54 may be referred to herein as "the vertical adjustment screws (46, 50, 54)." The anterior support arm 48, first posterior support arm 52, and second posterior support arm 56 may collectively be referred to herein as "the support arms (48, 52, 56)." Each of the vertical adjustment screws (46, 50, 54) may be spring-loaded to provide a spring-assisted return to level positioning of the top plates (16, 20, 24). The vertical adjustment screws (46, 50, 54) may be freely rotatable by any means known in the art of vises, such as by a collar and retaining ring or bearing block, among others.

Still referring to FIGS. 2A-C, the apparatus 10 further includes an anterior locking screw 58, a first posterior locking screw 60, and a second posterior locking screw 62, which are respectively mounted to the anterior ball joint 34, first posterior ball joint 36, and second posterior ball joint 38. The anterior locking screw 58, first posterior locking screw 60, and second posterior locking screw 62 may collectively be referred to herein as "the locking screws (58, 60, 62)". The locking screws (58, 60, 62) serve to prevent their respective ball joints (34, 36, 38) from being adjusted once a desired position has been reached.

Figure 3:
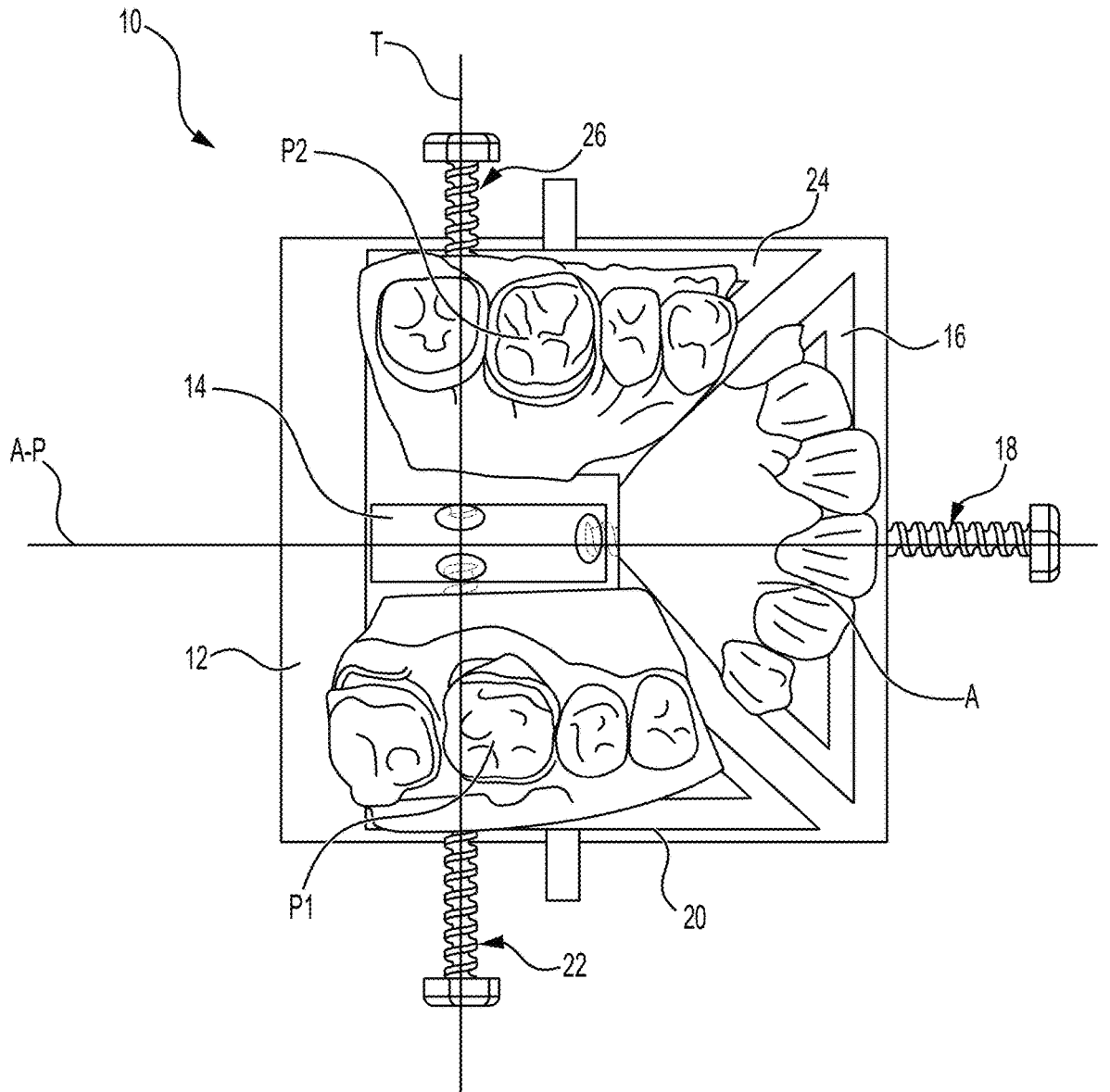
FIG. 3 is a top view of maxillary casts placed on an apparatus for orthognathic surgical planning.

The apparatus 10 disclosed herein is particularly advantageous for precise alignment and stabilization of three-piece maxillary segments during orthognathic surgical planning, as well as potential precise alignment and stabilization during orthognathic surgical procedures. With reference to FIG. 3, in pre-surgical planning, segmented maxillary casts including anterior segment A, first posterior segment P1 and second posterior segment P2 (collectively referred to as "the maxillary casts (A, P1, P2)") are placed respectively on the anterior plate 16, first posterior plate 20, and second posterior plate 24 of the apparatus 10. The maxillary casts (A, P1, P2) may be fitted with magnets thereon for attachment with the magnets (28, 30, 32) of the top plates (16, 20, 24).

Transverse adjustments are made to the positions along the transverse axis T of the first posterior segment P1 and the second posterior segment P2 using the respective first posterior screw 22 and second posterior screw 26. The anterior segment A is moved along the anterior posterior axis A-P through rotation of the anterior adjustment screw 18. The vertical adjustment screws (46, 50, 54), together with the ball joints (34, 36, 38), permit multi-dimensional movement of the top plates (16, 20, 24). Once the maxillary casts (A, P1, P2) are aligned in a desired position with a mandible cast (not shown), the casts are able to be fixed in the desired position by fastening of the ball joints (34, 36, 38) through the locking screws (58, 60, 62). Unlike manual manipulation of three-piece maxillary segments, which are prone to cumulative errors, misalignment and inaccuracies, the apparatus 10 provided herein ensures precision and repeatability, reduces surgical planning time, and improves functional and aesthetic outcomes.

It is to be understood that the apparatus for orthognathic surgical planning is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. An apparatus for orthognathic surgical planning, comprising:
 a base plate;
 a central pillar mounted to the base plate;
 an anterior plate;
 an anterior screw extending through the anterior plate into the central pillar, wherein the anterior plate is linearly movable along the anterior screw by rotation of the anterior screw, and wherein a length of the anterior screw extends along an anterior-posterior axis;
 a first posterior plate;
 a first posterior screw extending through the first posterior plate into the central pillar, wherein the first posterior plate is linearly movable along the first posterior screw by rotation of the first posterior screw, and wherein a length of the first posterior screw extends along a transverse axis orthogonal to the anterior-posterior axis;
 a second posterior plate;
 a second posterior screw extending through the second posterior plate into the central pillar, wherein the second posterior plate is linearly movable along the second posterior screw by rotation of the second posterior screw, and wherein a length of the second posterior screw extends along the transverse axis.

2. The apparatus for orthognathic surgical planning according to claim 1, further comprising:
 an anterior ball joint, wherein the anterior plate is mounted on the anterior ball joint;
 a first posterior ball joint, wherein the first posterior plate is mounted on the first posterior ball joint;
 a second posterior ball joint, wherein the second posterior plate is mounted on the second posterior ball joint.

3. The apparatus for orthognathic surgical planning according to claim 2, further comprising:
 an anterior sliding track, wherein the anterior ball joint is mounted on the anterior sliding track;
 a first posterior sliding track, wherein the first posterior ball joint is mounted on the first posterior sliding track;
 a second posterior sliding track, wherein the second posterior ball joint is mounted to the second posterior sliding track.

4. The apparatus for orthognathic surgical planning according to claim 3, further comprising:
 an anterior locking screw, wherein the anterior locking screw is configured to hold the anterior ball joint in a fixed position;
 a first posterior locking screw, wherein the first posterior locking screw is configured to hold the first posterior ball joint in a fixed position;
 a second posterior locking screw, wherein the second posterior locking screw is configured to hold the second posterior ball joint in a fixed position.

5. The apparatus for orthognathic surgical planning according to claim 4, further comprising:
 an anterior vertical adjustment screw and an anterior support arm, wherein the anterior support arm is mounted to the anterior ball joint, and wherein the anterior vertical adjustment screw is freely rotatable within a bottom surface of the anterior plate and is in threaded engagement with the anterior support arm;
 a first posterior vertical adjustment screw and a first posterior support arm, wherein the first posterior support arm is mounted to the first posterior ball joint, and wherein the first posterior vertical adjustment screw is freely rotatable within a bottom surface of the first posterior plate and is in threaded engagement with the first posterior support arm;
 a second posterior vertical adjustment screw and a second posterior support arm, wherein the second posterior support arm is mounted to the second posterior ball joint, and wherein the second posterior vertical adjustment screw is freely rotatable within a bottom surface of the second posterior plate and is in threaded engagement with the second posterior support arm.

6. The apparatus for orthognathic surgical planning according to claim 5, wherein the anterior vertical adjustment screw, the first posterior vertical adjustment screw, and the second posterior vertical adjustment screw are each spring-loaded.

7. The apparatus for orthognathic surgical planning according to claim 3, wherein the anterior sliding track, the first posterior sliding track, and the second posterior sliding track are each mounted to the central pillar.

8. The apparatus for orthognathic surgical planning according to claim 1, further comprising:

an anterior magnet on a top face of the anterior plate;

a first posterior magnet on a top face of the first posterior plate;

a second posterior magnet on a top face of the second posterior plate.

9. An apparatus for orthognathic surgical planning, comprising:

a base plate;

an anterior plate;

an anterior screw extending through the anterior plate, wherein the anterior screw includes a proximal end configured to be rotated by hand and a freely rotatable distal end anchored to at least one pillar extending from the base, wherein the anterior plate is linearly movable along the anterior screw by rotation of the anterior screw, and wherein a length of the anterior extends along an anterior-posterior axis;

a first posterior plate;

a first posterior screw extending through the first posterior plate, wherein the first posterior screw includes a proximal end configured to be rotated by hand and a freely rotatable distal end anchored to at least one pillar extending from the base, wherein the first posterior plate is linearly movable along the first posterior screw by rotation of the first posterior screw, and wherein a length of the first posterior screw extends along a transverse axis orthogonal to the anterior-posterior axis;

a second posterior plate;

a second posterior screw extending through the second posterior plate, wherein the second posterior screw includes a proximal end configured to be rotated by hand and a freely rotatable distal end anchored to at least one pillar extending from the base, wherein the second posterior plate is linearly movable along the second posterior screw by rotation of the second posterior screw, and wherein a length of the second posterior screw extends along the transverse axis.

* * * * *